(12) United States Patent  (10) Patent No.: US 9,044,549 B2
Niklasson  (45) Date of Patent: Jun. 2, 2015

(54) SYRINGE DISPENSER, STAND AND APPLICATION PLATE FOR SAID SYRINGE DISPENSER AND METHOD FOR ITS USE

(75) Inventor: Bo Niklasson, Malmö (SE)

(73) Assignee: NOVISCENS AB, Vellinge (SE)

( * ) Notice: Subject to any disclaimer, the term of this patent is extended or adjusted under 35 U.S.C. 154(b) by 0 days.

(21) Appl. No.: 13/639,988

(22) PCT Filed: Apr. 19, 2011

(86) PCT No.: PCT/SE2011/050478
§ 371 (c)(1),
(2), (4) Date: Oct. 23, 2012

(87) PCT Pub. No.: WO2011/133097
PCT Pub. Date: Oct. 27, 2011

(65) Prior Publication Data
US 2013/0043282 A1  Feb. 21, 2013

Related U.S. Application Data

(60) Provisional application No. 61/325,974, filed on Apr. 20, 2010.

(30) Foreign Application Priority Data

Apr. 20, 2010  (SE) ...................................... 1050389

(51) Int. Cl.
*B67D 7/60*  (2010.01)
*A61M 5/315*  (2006.01)
(Continued)

(52) U.S. Cl.
CPC ........... *A61M 5/31586* (2013.01); *A61M 5/007* (2013.01); *A61M 5/008* (2013.01); *A61M 5/3137* (2013.01); *A61M 2005/3139* (2013.01)

(58) Field of Classification Search
CPC ........... A61M 5/31528; A61M 5/3158; A61C 9/0026; B05C 17/00513; B05C 17/0133
USPC ............ 222/386, 390, 71, 309; 206/364, 366, 206/571, 443, 370, 557; 433/90, 89; 604/207, 209, 210, 211, 224, 218, 604/241–243, 187, 154; 211/126.1–126.7, 211/126.14, 60.1, 194, 88.01
See application file for complete search history.

(56) References Cited

U.S. PATENT DOCUMENTS 1,164,430 A * 12/1915 Thurman ....................... 604/218
1,555,711 A *  9/1925 Hershinger ................... 222/327
(Continued)

FOREIGN PATENT DOCUMENTS

EP  0265876 A2  5/1988
EP  1449551 A1  8/2004
(Continued)

*Primary Examiner* — Paul R Durand
*Assistant Examiner* — Randall Gruby
(74) *Attorney, Agent, or Firm* — Capitol City TechLaw

(57) ABSTRACT

A syringe dispenser may include a plunger having an outer threading, a barrel adapted to contain liquid or semisolid fluid or any other material to be dispensed and to receive the plunger, the plunger being movably attached to the barrel, and a nut having an inner threading. The nut may at least partly enclose the plunger and the barrel, such that the inner threading of the nut engages with the outer threading of the plunger. A stand, an application plate, and a method of dispensing a controlled and measurable amount of liquid or semisolid fluid from a syringe dispenser are also disclosed.

13 Claims, 4 Drawing Sheets

(51) Int. Cl.
*A61M 5/31* (2006.01)
*A61M 5/00* (2006.01)

(56) References Cited

U.S. PATENT DOCUMENTS

| | | | |
|---|---|---|---|
| 1,644,173 A * | 10/1927 | Carr | 222/390 |
| 2,459,921 A * | 1/1949 | Comer | 220/512 |
| 2,557,420 A * | 6/1951 | Elliott | 206/366 |
| 2,745,575 A * | 5/1956 | Spencer | 222/327 |
| 2,853,070 A * | 9/1958 | Julliard | 604/224 |
| 3,212,685 A * | 10/1965 | Swan et al. | 222/386 |
| D208,192 S * | 8/1967 | Seymour | D24/230 |
| 3,349,937 A * | 10/1967 | Duff et al. | 217/25.5 |
| 3,353,718 A * | 11/1967 | McLay | 222/158 |
| 3,643,812 A * | 2/1972 | Mander et al. | 211/74 |
| 3,669,111 A * | 6/1972 | Dubner | 604/229 |
| 3,682,323 A * | 8/1972 | Bergquist et al. | 211/74 |
| 3,737,973 A * | 6/1973 | Stawski | 29/407.1 |
| 3,767,085 A * | 10/1973 | Cannon et al. | 222/82 |
| 4,153,056 A | 5/1979 | Silver et al. | |
| 4,189,065 A | 2/1980 | Herold | |
| 4,246,898 A | 1/1981 | Travalent et al. | |
| 4,269,331 A * | 5/1981 | Watson | 222/390 |
| 4,275,729 A * | 6/1981 | Silver et al. | 604/211 |
| 4,312,343 A * | 1/1982 | LeVeen et al. | 604/211 |
| 4,397,647 A * | 8/1983 | Gordon | 604/180 |
| 4,498,904 A * | 2/1985 | Turner et al. | 604/211 |
| 4,568,335 A * | 2/1986 | Updike et al. | 604/211 |
| 4,601,711 A * | 7/1986 | Ashbury et al. | 604/229 |
| 4,710,179 A | 12/1987 | Haber et al. | |
| 4,723,948 A * | 2/1988 | Clark et al. | 604/533 |
| 4,774,772 A * | 10/1988 | Vetter et al. | 34/105 |
| 4,852,768 A * | 8/1989 | Bartsch | 222/46 |
| 4,974,752 A * | 12/1990 | Sirek | 222/146.5 |
| 5,011,028 A * | 4/1991 | Sweeney | 211/60.1 |
| 5,059,181 A * | 10/1991 | Agran | 604/110 |
| 5,279,586 A * | 1/1994 | Balkwill | 604/207 |
| 5,290,260 A * | 3/1994 | Stines | 604/224 |
| 5,306,248 A * | 4/1994 | Barrington | 604/97.02 |
| 5,311,985 A * | 5/1994 | Suida | 206/210 |
| 5,318,544 A | 6/1994 | Drypen et al. | |
| 5,344,409 A | 9/1994 | Ennis, III et al. | |
| 5,372,252 A * | 12/1994 | Alexander | 206/210 |
| 5,599,311 A * | 2/1997 | Raulerson | 604/175 |
| 5,618,273 A * | 4/1997 | Fischer | 604/211 |
| 5,700,247 A * | 12/1997 | Grimard et al. | 604/220 |
| 5,728,075 A * | 3/1998 | Levander | 604/211 |
| 5,823,363 A * | 10/1998 | Cassel | 211/60.1 |
| 5,850,917 A * | 12/1998 | Denton et al. | 206/366 |
| 5,865,805 A * | 2/1999 | Ziemba | 604/154 |
| 6,004,298 A | 12/1999 | Levander | |
| D419,671 S * | 1/2000 | Jansen | D24/112 |
| 6,367,962 B1 * | 4/2002 | Mizutani et al. | 366/189 |
| 6,371,938 B1 * | 4/2002 | Reilly et al. | 604/131 |
| 6,419,086 B1 * | 7/2002 | Vecchio | 206/366 |
| 6,520,381 B1 * | 2/2003 | Prestele | 222/137 |
| D474,274 S * | 5/2003 | Walters | D24/130 |
| 6,562,007 B1 * | 5/2003 | Falsey | 604/211 |
| 6,638,065 B2 * | 10/2003 | Fischer et al. | 433/89 |
| 6,712,794 B2 * | 3/2004 | Kust et al. | 604/224 |
| D496,541 S * | 9/2004 | Wang | D6/466 |
| 6,793,660 B2 * | 9/2004 | Kerr et al. | 606/93 |
| 6,916,308 B2 * | 7/2005 | Dixon et al. | 604/122 |
| 6,955,259 B1 * | 10/2005 | Jesse | 206/366 |
| 7,169,361 B2 * | 1/2007 | Arnold et al. | 422/526 |
| 7,392,735 B2 * | 7/2008 | Brass et al. | 92/32 |
| 7,419,478 B1 * | 9/2008 | Reilly et al. | 604/241 |
| 7,530,970 B2 * | 5/2009 | McArthur et al. | 604/208 |
| D621,639 S * | 8/2010 | Merrick | D6/469 |
| 7,901,384 B2 * | 3/2011 | Kleyman et al. | 604/207 |
| 7,954,672 B2 * | 6/2011 | Keller | 222/137 |
| 7,976,510 B2 * | 7/2011 | Janish et al. | 604/218 |
| 8,100,263 B2 * | 1/2012 | Vanderbush et al. | 206/524.8 |
| 8,394,068 B2 * | 3/2013 | Kosinski et al. | 604/219 |
| 8,460,622 B2 * | 6/2013 | Motadel | 422/564 |
| 8,470,267 B2 * | 6/2013 | Holenstein et al. | 422/549 |
| 8,590,747 B2 * | 11/2013 | Keller | 222/137 |
| 2001/0011163 A1 * | 8/2001 | Nolan et al. | 604/154 |
| 2002/0068257 A1 * | 6/2002 | Albach | 433/89 |
| 2003/0004467 A1 * | 1/2003 | Musick et al. | 604/218 |
| 2003/0040718 A1 * | 2/2003 | Kust et al. | 604/224 |
| 2004/0216591 A1 * | 11/2004 | Assadi et al. | 89/1.14 |
| 2005/0101905 A1 | 5/2005 | Merry | |
| 2005/0131354 A1 * | 6/2005 | Tachikawa et al. | 604/187 |
| 2005/0284784 A1 * | 12/2005 | Chen | 206/366 |
| 2006/0131344 A1 * | 6/2006 | Brass | 222/390 |
| 2007/0072146 A1 * | 3/2007 | Pierson | 433/90 |
| 2008/0147014 A1 * | 6/2008 | Lafferty | 604/191 |
| 2008/0289973 A1 * | 11/2008 | MacLeod | 206/81 |
| 2009/0026107 A1 * | 1/2009 | Ross | 206/570 |
| 2009/0026108 A1 * | 1/2009 | Ross | 206/570 |
| 2010/0089938 A1 * | 4/2010 | Motadel | 221/1 |
| 2011/0087173 A1 * | 4/2011 | Sibbitt et al. | 604/207 |
| 2011/0125088 A1 * | 5/2011 | Dixon et al. | 604/82 |
| 2012/0197211 A1 * | 8/2012 | Brister et al. | 604/207 |
| 2012/0244493 A1 * | 9/2012 | Leiner et al. | 433/90 |
| 2014/0012229 A1 * | 1/2014 | Bokelman et al. | 604/506 |
| 2014/0263403 A1 * | 9/2014 | Conner et al. | 222/1 |
| 2014/0276581 A1 * | 9/2014 | Lou et al. | 604/506 |
| 2014/0330213 A1 * | 11/2014 | Hourmand et al. | 604/187 |

FOREIGN PATENT DOCUMENTS

| | | |
|---|---|---|
| WO | 9907421 | 2/1999 |
| WO | 2005097239 A1 | 10/2005 |
| WO | 2007041266 A1 | 4/2007 |

* cited by examiner

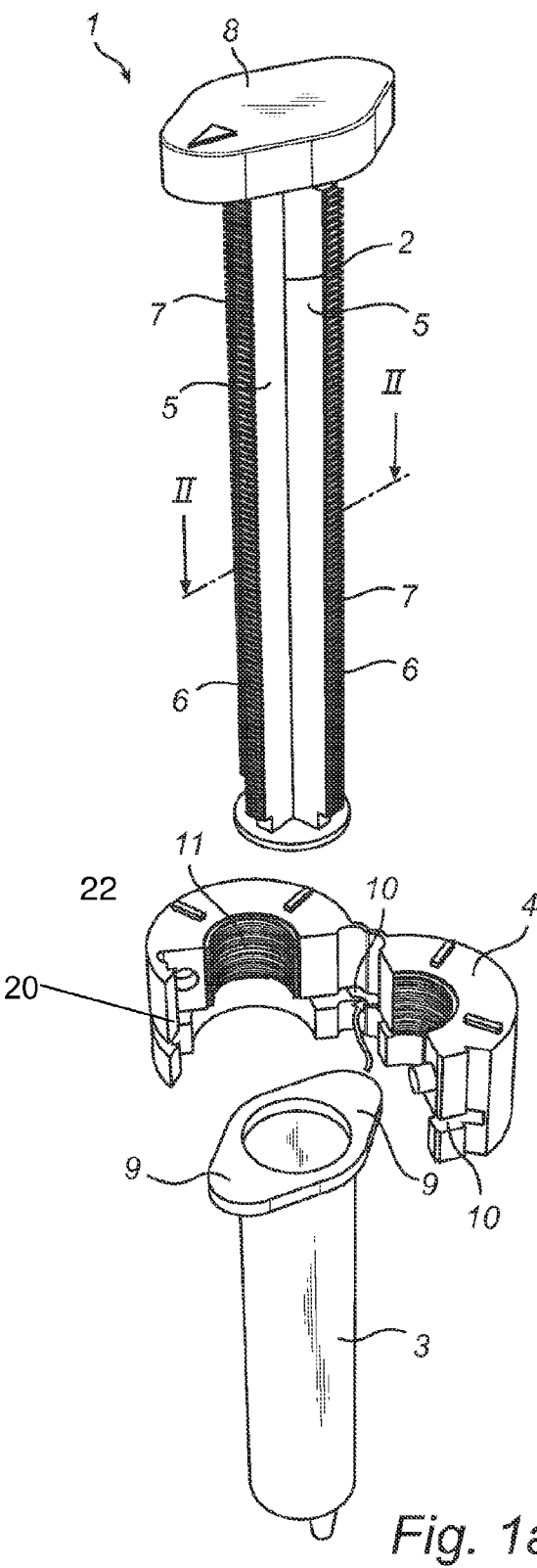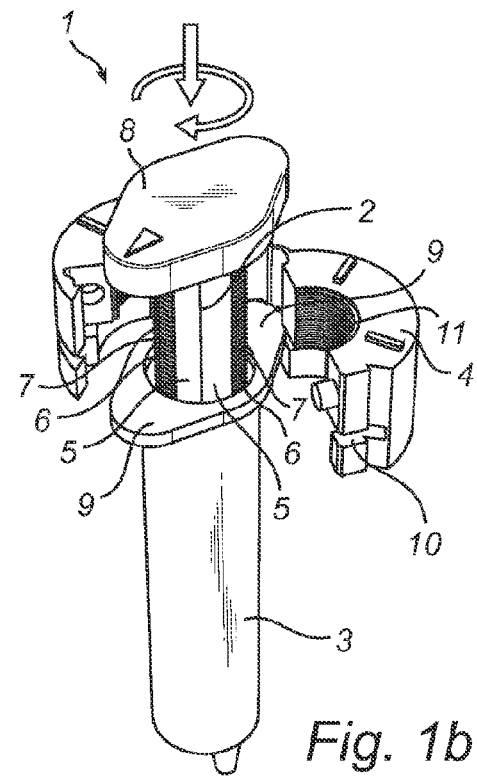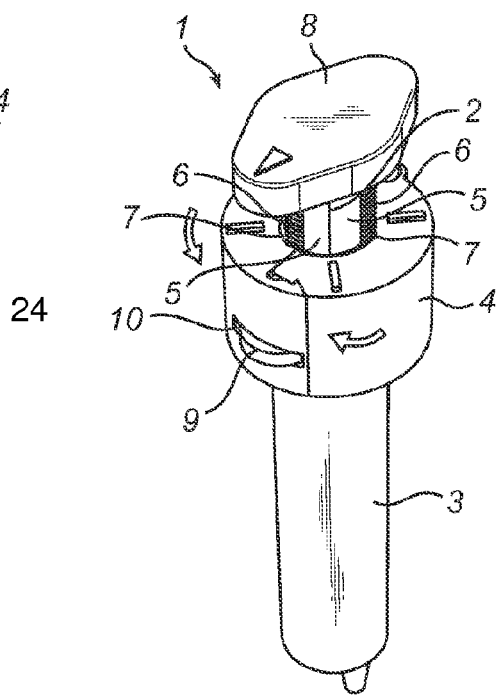
Fig. 1a
Fig. 1b
Fig. 1c

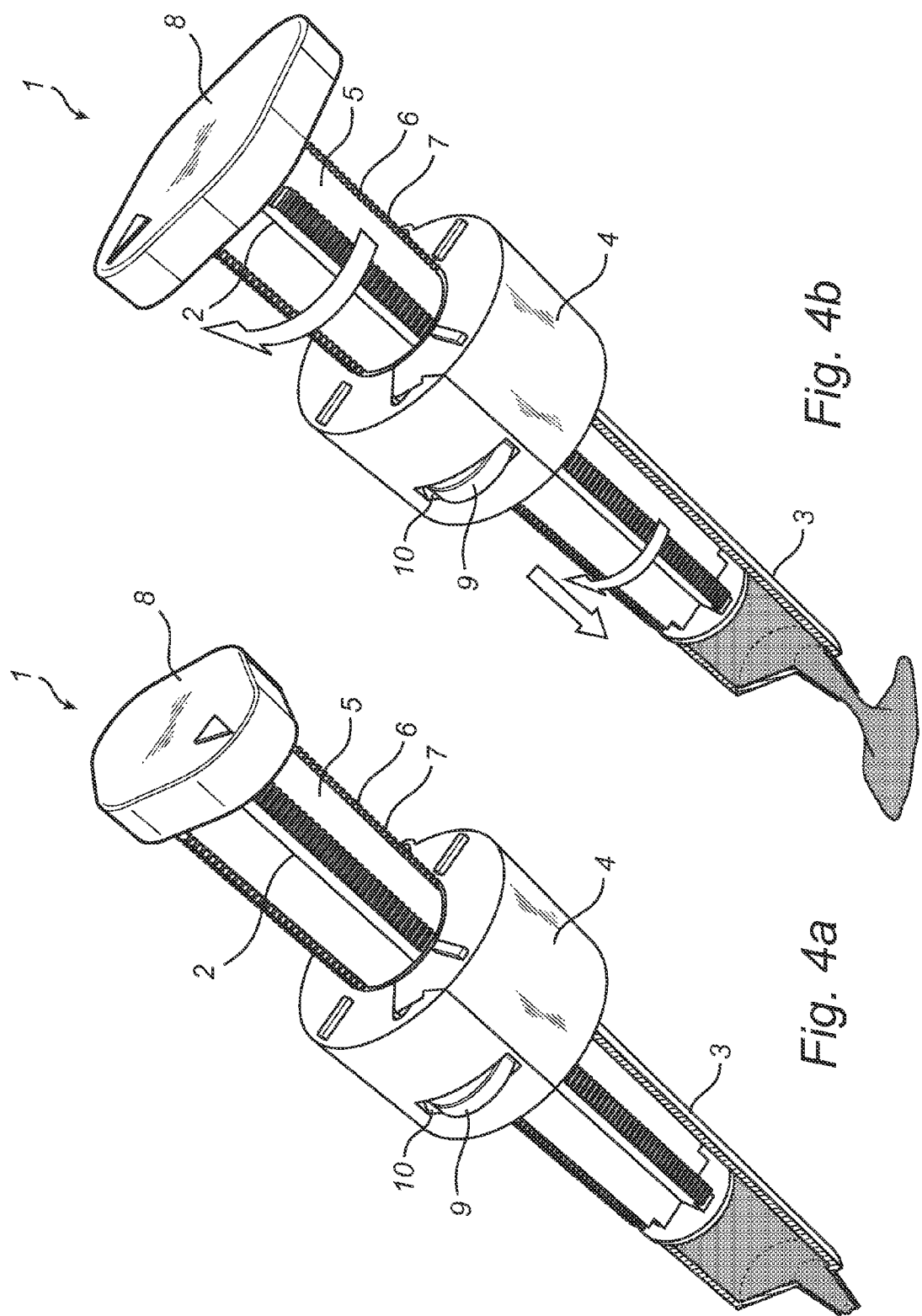

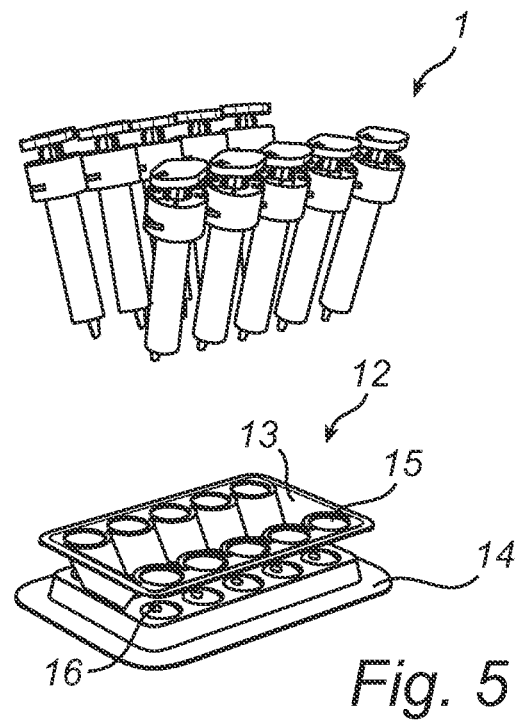
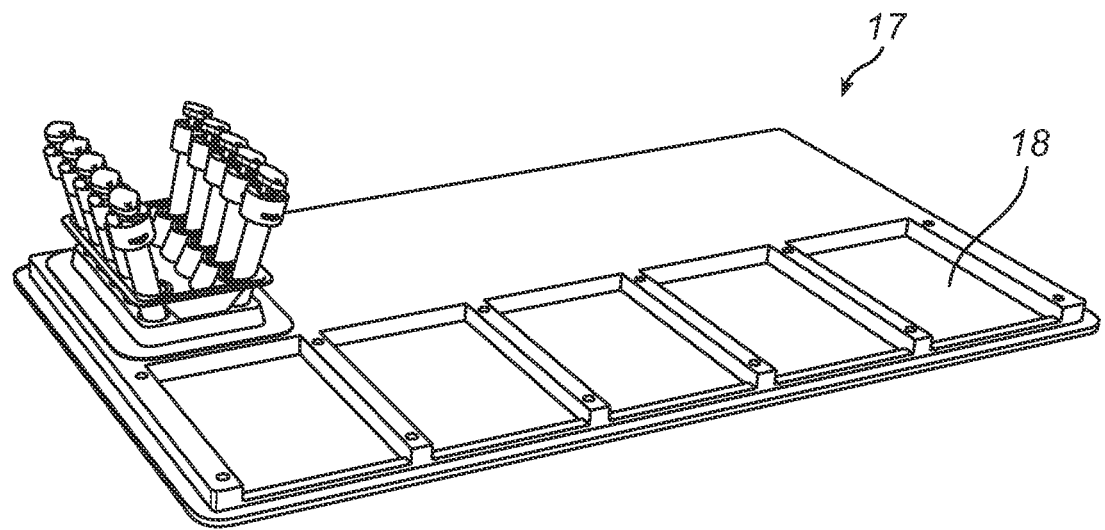
Fig. 5
Fig. 6

SYRINGE DISPENSER, STAND AND APPLICATION PLATE FOR SAID SYRINGE DISPENSER AND METHOD FOR ITS USE

TECHNICAL FIELD

The present invention relates to a syringe dispenser, comprising a plunger having an outer threading, a barrel adapted to contain liquid or semisolid fluid or any other material to be dispensed and to receive said plunger, said plunger being movably attached to said barrel, and a nut having an inner threading. The invention also relates to a stand, an application plate, and a method of dispensing a controlled and measurable amount of liquid or semisolid fluid from a syringe dispenser.

BACKGROUND ART

Syringes commonly used in various application areas do not utilize a more precise dosing function beyond the grading in milliliter that normally is present on the barrel of the syringe. The dose provided by the person pressing the plunger is therefore not precise and is influenced by the skill of the user. In some application areas a precise and accurate dose is important and will in cases of various treatments of diseases increase the therapeutic accuracy, safety and efficacy of the treatment. In areas where a diagnostic application is used, such as in vitro or in vivo testing, exemplified by patch testing in contact dermatitis, an accurate and quantified dose will provide a higher accuracy and validity of the method. In this diagnostic procedure a dose of a hapten (test preparation) is applied onto a test chamber mounted on a strip of tape that is subsequently applied onto the patients back. The dose that is applied using a graded syringe is not precise and may vary by a factor of at least 1 to 3 using current techniques. Achieving a precise dose will not only result in an increased accuracy of the method in individual patient investigations but will also result in a higher validity in coordinated clinical multicenter studies as the elicitation and intensity of the clinical immunological reaction is dependant on the dose given. The results in the different clinics can therefore be accurately compared as the same dispensing volume is applied. Similarly it is important when administering certain medications to a patient that the volume is known so that the patient is safely treated without risk for overdosage of the medication resulting in adverse side effects and serious medical conditions or underdosage resulting in lack of achieved effect. Likewise, when administering dental materials it is of importance to provide a predetermined controlled dose in order to give the patient an accurate treatment. Accordingly, the unsatisfying accuracy of the syringes used today constitutes a problem when used in situations as mentioned above.

Previous inventions have not been able to teach an inexpensive, easy to use, prefilled or unfilled syringe that allows the physician or other user to accurately dispense a quantified volume of sterile or unsterile, viscous or non-viscous material by using a screwable syringe device dispensing material via a rotational movement of the plunger. A few attempts have been made to provide some of these desired features by way of combining special metering devices with the conventional syringe and other attempts have required the conventional syringe cylinder to be modified. Unfortunately, the ability to dispense a controlled calibrated dose of a material by using such a mode of action has not been successful.

Another drawback of the present dispensing technique using a syringe with a traditional plunger and barrel is in the ergonomical area. After some time, a nurse or other personnel using today's technique may develop pain in the thumb and hand due to the repeated pressing of the plunger and wear may also occur resulting in absence from work and sick leave due to this kind of work related disease.

SUMMARY OF THE INVENTION

It is an object of the present invention to provide an improvement of the above techniques and prior art. More particularly, it is an object of the present invention to provide an improved syringe dispenser able to dispense a controlled and measurable amount of liquid or semisolid fluid and at the same time avoid ergonomical work related diseases. Further, it is an object of the present invention to provide a stand, an application plate and a method of dispensing a controlled and measurable amount of liquid or semisolid fluid from a syringe dispenser.

These and other objects as well as advantages that will be apparent from the following description of the present invention are achieved by a syringe dispenser according to the independent claim.

A syringe dispenser is provided. The syringe dispenser comprises a plunger having an outer threading, a barrel adapted to contain liquid or semisolid fluid or any other material to be dispensed and to receive said plunger, said plunger being movably attached to the barrel, and a nut having an inner threading. The nut is at least partly enclosing the plunger and the barrel, such that the inner threading of said nut engage with the outer threading of the plunger. This is advantageous in that a very accurate dispensing volume will be achieved by using the syringe dispenser. By rotating the plunger in a clockwise downward direction after the barrel has been filled with the material to be dispensed, the plunger will press the material to be dispensed out of the tip of the barrel. The syringe dispenser dispenses, via a screwable action in a continuous mode, controlled and calibrated volumes of either sterile or unsterile, viscous or non-viscous material such as drug medications, diagnostic preparations for various purposes such as in the diagnosis of allergic diseases showing immediate or delayed type reactions, radioactive or other labelled substances, dental materials, substances used in analytical chemistry, or in any other application where a controlled volume to be dispensed is desired. The controlled volume is achieved through calculating the relation between the pitch of the threaded nut combined with the threaded plunger and correlated to the number of rotations or part of rotation of the plunger. The rotations of the plunger are measured by observing indicia on the ledge of the plunger shaft compared with indicia on the nut. Also, by using a rotating movement as described above instead of a pressing action, less force is applied and less motion of the fingers is used and therefore such work related diseases may be avoided.

The barrel may have a flange extending in a perpendicular direction to the longitudinal direction of said barrel, and the nut may have a recess adapted to receive said flange of said barrel. When the nut is applied onto the barrel and plunger, the flange of the barrel enters into the corresponding recess in the nut in order to prevent the nut from getting dislocated, especially when the plunger is rotated.

The nut may be a snap-on nut being releasably attached to said plunger and said barrel. Accordingly, the snap-on nut may not be attached to the syringe barrel and plunger when delivered and the syringe can therefore be filled by the user. The preferred way to fill the syringe with material and to avoid air space between the plunger and material, is to either use pressure or suction and fill material from the bottom of the barrel through the tip of the syringe.

The outer threading may extend in the longitudinal direction of the plunger, which may have a plurality of side walls extending in a perpendicular direction to the longitudinal direction of said plunger. This is advantageous in that the interaction between the plunger and the barrel is given stability and structure.

The cross section of said plunger may be cruciform, which is one embodiment of the invention.

The outer threading may be arranged on an outer surface of each side wall of said plunger, which simplifies the engagement with the inner threading of the nut. The inner threading may extend in the longitudinal direction of the nut.

The plunger may have a top having a marking corresponding to a marking of the nut. This is advantageous in that by relating the marking of the top to the marking of the nut, the user of the syringe will know exactly the volume of liquid or semisolid fluid dispensed. The controlled volume is achieved through calculating the relation between the pitch of the threaded nut combined with the threaded plunger and correlated to the number of rotations or part of rotation of the plunger.

The plunger may have a seal attached to the bottom of said plunger for sealing said plunger against the inner wall surface of said barrel in order to reduce the risk of leakage.

The syringe dispenser may further comprise a cap releasably attached to the tip of said syringe dispenser in order to prevent leakage from the tip of the barrel.

According to a second aspect of the invention, the invention relates to a stand for supporting syringe dispensers, comprising an upper section having a plurality of through holes, each through hole being adapted to receive a syringe dispenser according to the above described features, and a lower section having a plurality of through holes, each through hole being adapted to receive a tip of said syringe dispenser.

According to a third aspect of the invention, the invention relates to an application plate, comprising a plurality of compartments, each compartment being adapted to receive a patch testing chamber unit or other material receiving unit, and means for releasably attaching a stand according to the above described features above each compartment, such that said patch testing chamber unit or said other material receiving unit may be filled by liquid or semisolid fluids contained in syringe dispensers supported by said stand.

According to a fourth aspect of the invention, the invention relates to method of dispensing a controlled and measurable amount of liquid or semisolid fluid from a syringe dispenser. The method comprises providing a plunger having an outer threading, providing a barrel containing liquid or semisolid fluid, movably attaching said plunger to said barrel, arranging a nut having an inner threading around said plunger and said barrel, engaging said inner threading of said nut with said outer threading of said plunger, and rotating said plunger in relation to said nut and said barrel a certain distance, whereby a controlled and measurable amount of liquid or semisolid fluid corresponding to said distance is dispensed from said syringe dispenser.

It should be noted that the inventive method may incorporate any of the features described above in connection with the inventive syringe dispenser, stand and application plate and have the same respective advantages.

Generally, all terms used in the claims are to be interpreted according to their ordinary meaning in the technical field, unless explicitly defined otherwise herein. All references to "a/an/the [element, device, component, means, etc]" are to be interpreted openly as referring to at least one instance of said element, device, component, means, etc., unless explicitly stated otherwise.

BRIEF DESCRIPTION OF THE DRAWINGS

The above, as well as additional objects, features and advantages of the present invention, will be better understood through the following illustrative and non-limiting detailed description of preferred embodiments of the present invention, with reference to the appended drawings, where the same reference numerals will be used for similar elements, wherein:

FIGS. 1a-c are perspective views of a syringe dispenser according to one embodiment of a first aspect of the invention ranging from unassembled to assembled.

FIGS. 4a-b are perspective views of the syringe dispenser when assembled and containing liquid or semisolid fluid, FIG. 5 is a perspective view of a stand according to a second aspect of the invention, and FIG. 6 is a perspective view of an application plate according to a third aspect of the invention.

DETAILED DESCRIPTION OF PREFERRED EMBODIMENTS OF THE INVENTION

Figure 2:
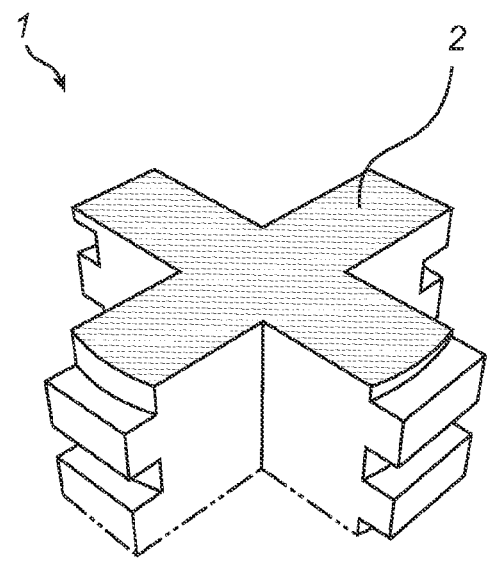
FIG. 2 is a cross section of the plunger.

FIGS. 1a-c illustrate a syringe dispenser 1 according to one embodiment of a first aspect of the invention. The syringe dispenser 1 comprises a plunger 2, a barrel 3 and a nut 4. The plunger 2 has four side walls 5 extending in a perpendicular direction to the longitudinal direction of the plunger 2. On an outer surface 6 of each side wall 5, an outer threading 7 is provided extending in the longitudinal direction of the plunger 2. The plunger 2 further has a top 8 with a marking corresponding to a marking of the nut 4. The barrel 3 is adapted to contain liquid or semisolid fluid and to receive the plunger 2, as illustrated in FIGS. 1b and 1c, such that the plunger 2 becomes movably attached to the barrel 3. The barrel 3 has two flanges 9 extending in a perpendicular direction to the longitudinal direction of the barrel 3, which are corresponding to two recesses 10 of the nut 4. The nut 4 is a snap-on nut adapted to be releasably arranged to the plunger 2 and the barrel 3, and has an inner threading 11 extending in the longitudinal direction of the nut 4. When the syringe dispenser 1 is being assembled, the plunger 2 is placed in the barrel 3 and the nut 4 is attached to the plunger 2 and the barrel 3 such that the two flanges 9 of the barrel 3 are arranged in the two recesses 10 of the nut 4. When the nut 4 is enclosing the plunger 2 and the barrel 3, the inner threading 11 of the nut 4 engage with the outer threading 7 of the plunger 2.

In FIG. 2, a cross section of the plunger 2 is illustrated. The cross section of the plunger 2 is cruciform.

Figure 3A:
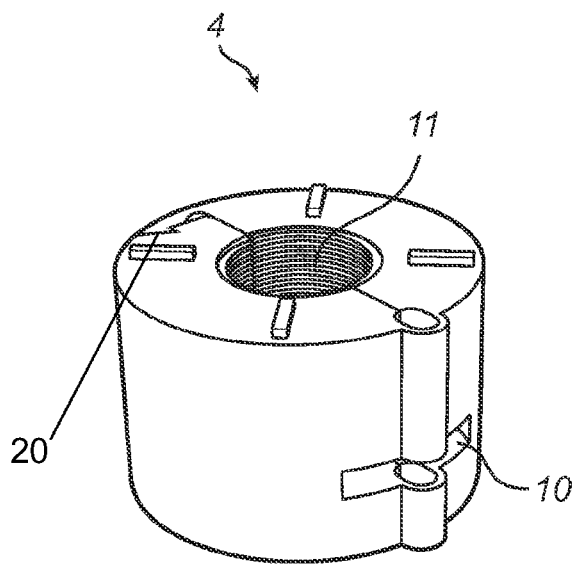
FIGS. 3a-b are perspective views of a nut of the invention.
Figure 3B:
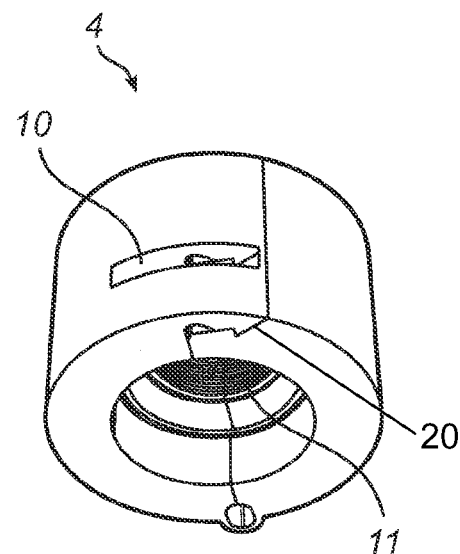

FIGS. 3a and 3b illustrate the nut 4 of the syringe dispenser 1. The nut 4 is a snap-on nut and may accordingly be opened in order to be placed around the plunger 2 and the barrel 3 of the syringe dispenser 1. The nut 4 is made in one part with two half cylindrical parts connected by a type of hinge with a snap-on function as well as click function that locks the nut 4, with an inner threaded 11 area facing each other when the nut 4 has been closed embracing the threaded plunger 2. The angle and pitch of the threading will determine the dose that is applied.

The half cylindrical parts of the nut 4 have respective parting faces that are exposed when the nut 4 is opened. One of the parting faces includes a ramped surface 20 and a blind hole 22. The blind hole 22 is located closer to the longitudinal center axis of the nut 4 than the ramped surface 20. In the closed condition (as shown in FIG. 1c for example), the ramped surface 20 is inclined relative to a radial direction of the nut 4. As the nut 4 is closed around the plunger 2 and the barrel 3 (i.e., moving from the opened condition shown in FIG. 1b to the closed condition shown in FIG. 1c) the ramped surface 20 slides across the opposing parting face of the nut 4. During this time, a guide post 24 provided on the opposing parting face enters into the blind hole 22.

In FIGS. 4a and 4b, the syringe dispenser 1 when assembled and containing liquid or semisolid fluid is illustrated. When using the syringe dispenser 1, the plunger 2 is rotated in relation to the nut 4 and the barrel 3 at a certain distance. Due to the engagement between the outer threading 7 of the plunger 2 and the inner threading 11 of the nut 4, the plunger 2 is forced downwards in the longitudinal direction of the syringe dispenser 1 in relation to the barrel 3 and the nut 4, thereby pressing the material to be dispensed out of the tip of the barrel 3. By controlling the angle and pitch of the threading, the exact dose dispensed can be determined. Accordingly, an exact, controlled and measurable amount of material corresponding to the distance the plunger 2 has been rotated will be dispensed from the syringe dispenser 1.

FIG. 5 illustrates a stand 12 for supporting syringe dispensers 1 according to a second aspect of the invention. The stand 12 comprises an upper section 13 and a lower section 14. The upper section 13 has a plurality of through holes 15, each through hole 15 being adapted to receive the syringe dispenser 1 according to the above described features. The lower section 14 also has a plurality of through holes 16, each through 16 hole being adapted to receive the tip of the syringe dispenser 1.

In FIG. 6, an application plate 17 is illustrated. The application plate 17 comprises a plurality of compartments 18 being adapted to receive a patch testing chamber unit, and means for releasably attaching a stand 12 according to the above described features above each compartment 18. This way, the patch testing chamber unit may be filled by liquid or semisolid fluids contained in the syringe dispensers 1 supported by the stand 12.

The plunger may have a seal attached to the bottom of said plunger for sealing said plunger against the inner wall surface of said barrel in order to reduce the risk of leakage. Also, the syringe dispenser may further comprise a cap being releasably attached to the tip of said syringe dispenser in order to prevent leakage.

Areas of application for the invention include dispensing in diagnostic in vivo or in vitro methods such as allergy testing, dispensing of dental materials, dispensing of pharmaceutical materials in clinical treatments, dispensing of materials in cosmetic treatments, dispensing of materials for chemical analysis in i.e. HPLC, GC and other such analytical methods, industrial dispensing where an accurate volume is desired and in related areas where an accurate dispensing volume is needed.

The syringe dispenser may either be prefilled from the manufacturer in an industrial automated manner, using, depending on selected application, sterile or unsterile, viscous or non viscous preparations for various dispensing and dosing purposes, or unfilled so that the user may fill whatever material to be dispensed.

Material to be used for the production of the parts of the syringe dispenser may include various plastic materials. According to one embodiment, the present invention is made of polypropylene. Other materials to be used may be made of polycarbonate, polyethylene, nylon, Teflon or comparable suitable material.

The invention has mainly been described above with reference to a few embodiments. However, as is readily appreciated by a person skilled in the art, other embodiments than the ones disclosed above are equally possible within the scope of the invention, as defined by the appended claims.

The invention claimed is:

1. A syringe dispenser, comprising
a plunger having an outer threading;
a barrel adapted to contain a material to be dispensed and to receive the plunger, the plunger being movably attached to the barrel; and
a nut having an inner threading;
wherein the nut at least partly encloses the plunger and the barrel, such that the inner threading of the nut engages with the outer threading of the plunger;
wherein the nut is an openable snap-on nut being releasably attached to the plunger and the barrel, respectively;
wherein the nut is of a unitary, one-piece construction with two half cylindrical parts connected by a hinge;
wherein the half cylindrical parts have respective parting faces that are (1) exposed when the nut is opened about the hinge, and (2) unexposed in confrontation with each other when the nut is in a closed condition;
wherein a first one of the parting faces has
a ramped surface, such that a plane coincident with the ramped surface is spaced apart from a longitudinal center axis of the nut, and
a blind hole provided closer to the longitudinal center axis than the ramped surface; and
wherein a second one of the parting faces has a guide post that extends into the blind hole when he nut is in the dosed condition.

2. The syringe dispenser according to claim 1, wherein the barrel has a flange extending in a perpendicular direction to a longitudinal direction of the barrel.

3. The syringe dispenser according to claim 2, wherein the nut has a recess adapted to receive the flange of the barrel.

4. The syringe dispenser according to claim 1, wherein the outer threading extends in a longitudinal direction of the plunger.

5. The syringe dispenser according to claim 1, wherein the plunger has a plurality of side walls extending in a perpendicular direction to a longitudinal direction of the plunger.

6. The syringe dispenser according to claim 5, wherein a cross section of the plunger is cruciform.

7. The syringe dispenser according to claim 6, wherein the outer threading is arranged on an outer surface of each of the side walls of the plunger.

8. The syringe dispenser according to claim 1, wherein the inner threading extends in a longitudinal direction of the nut.

9. The syringe dispenser according to claim 1, wherein the plunger has a top having a marking corresponding to a marking of the nut.

10. The syringe dispenser according to claim 1, wherein a seal is attached to a bottom of the plunger for sealing the plunger against an inner wall surface of the barrel.

11. The syringe dispenser according to claim 1, further comprising a cap releasably attached to a tip of the syringe dispenser.

12. A method of dispensing a controlled and measurable amount of material from a syringe dispenser, the method comprising:
providing a plunger having an outer threading;
providing a barrel containing material;
movably attaching the plunger to the barrel;
releasably arranging an openable snap-on nut having an inner threading around the plunger and the barrel, respectively;
wherein the nut is of a unitary, one-piece construction with two half cylindrical parts connected by a hinge;

wherein the half cylindrical parts have respective parting faces that are (1) exposed when the nut is opened about the hinge, and (2) unexposed in confrontation with each other when the nut is in a closed condition;
wherein a first one of the parting faces has
a ramped surface, such that a plane coincident with the ramped surface is spaced apart from a longitudinal center axis of the nut, and
a blind hole provided closer to the longitudinal center axis than the ramped surface;
wherein a second one of the parting faces has a guide post that extends into the blind hole when the nut is in the closed condition;
engaging the inner threading of the nut with the outer threading of the plunger; and
rotating the plunger relative to the nut and the barrel a distance, such that a controlled and measurable amount of material corresponding to the distance is dispensed from the syringe dispenser.

13. The method according to claim 12, wherein upon arranging the nut around the plunger and the barrel, the ramped surface slides across the second parting face of the nut.

* * * * *